United States Patent [19]
Kikuchi et al.

[11] Patent Number: 4,841,989
[45] Date of Patent: Jun. 27, 1989

[54] APPLICATOR FOR USE IN HYPERTHERMIA

[75] Inventors: Makoto Kikuchi, Mitaka; Shinsaku Mori, Tokyo; Yoshio Nikawa, Tokyo; Takashige Terakawa, Tokyo, all of Japan

[73] Assignee: Tokyo Keiki Co., Ltd., Tokyo, Japan

[21] Appl. No.: 878,328

[22] Filed: Jun. 25, 1986

[30] Foreign Application Priority Data

Jun. 29, 1985 [JP] Japan ................. 60-143541
Jun. 29, 1985 [JP] Japan ................. 60-143542

[51] Int. Cl.⁴ ............................................. A61N 5/00
[52] U.S. Cl. ........................... 128/804; 219/10.55 F; 219/10.55 R
[58] Field of Search ................ 128/804, 399; 219/10.55 A, 10.55 F, 10.55 R

[56] References Cited

U.S. PATENT DOCUMENTS

| | | | |
|---|---|---|---|
| 3,065,752 | 11/1962 | Potzl | 128/804 X |
| 4,003,383 | 1/1977 | Bruck | 128/804 X |
| 4,108,147 | 8/1978 | Kantor | 128/804 |
| 4,140,130 | 2/1979 | Storm | 128/804 |
| 4,228,809 | 10/1980 | Paglione | 128/804 |
| 4,397,313 | 8/1983 | Vaguine | 128/399 |
| 4,397,314 | 8/1983 | Vaguine | 128/399 |
| 4,462,412 | 7/1984 | Turner | 128/804 |
| 4,586,516 | 5/1986 | Turner | 128/804 |
| 4,589,424 | 5/1986 | Vaguine | 128/804 |

FOREIGN PATENT DOCUMENTS

| | | | |
|---|---|---|---|
| 0111386 | 6/1984 | European Pat. Off. . | |
| 1440333 | 4/1969 | Fed. Rep. of Germany . | |
| 2508494 | 9/1976 | Fed. Rep. of Germany | 128/804 |
| 862646 | 3/1961 | United Kingdom | 128/804 |

OTHER PUBLICATIONS

Magin, IEEE Trans Microwave Theory and Tech., MTT 27, No. 1, pp. 78–83, Jan. 1979.
Robinson et al., IEEE Trans Microwave Theory and Tech, MTT 26, No. 8, pp. 546–549, Aug. 1978.
*Hyperthermia in Cancer Therapy*, Storm, G. K. Hull, Med. Pub., 1983.
Astrahan et al., IEEE Trans Microwave Theory and Tech., MTT 26, No. 18, pp. 546–549, Aug. 1978.

*Primary Examiner*—Lee S. Cohen
*Attorney, Agent, or Firm*—Sandler & Greenblum

[57] ABSTRACT

A very large proportion of electromagnetic waves are reflected by the surface of the human body. To cope with this phenonmenon, the applicator of the present invention incorporates an electromagnetic lens at an electromagnetic wave-radiating end portion thereof, thereby enabling electromagnetic waves propagated in the human body to be gradually focused into a portion of the body to be heated. An omnidirectional electromagnetic lens is employed.

Affected parts located at different depths in the body are generally treated by different applicators. However, the applicator of the present invention is constructed so that the electromagnetic lens is replacable. In consequence, only one case for the applicator is required. This makes the use of the applicator easier.

For the purpose of providing a small-sized electromagnetic lens and applicator, coolant is made to flow inside the electromagnetic lens. This is effective from the viewpoint of the electromagnetic wave transmission system as well as with a view to tuning impedance of the human body.

16 Claims, 10 Drawing Sheets

APPLICATOR FOR USE IN HYPERTHERMIA

BACKGROUND OF THE INVENTION

1. Field of the Invention

The present invention relates to an applicator for use in hyperthermia, and, more particularly, to an applicator for use in hyperthermia which is used to treat a predetermined position of a human body by locally applying heat thereto by means of electromagnetic waves. 2. Prior Art Lately, hyperthermia has been attracting attention. Recent reseaches (including that reported on Page 14 of MICROWAVES, October, 1976) have shown that, if heat is continuously applied to a malignant tumor at a temperature of about 43° C. for an hour or two, and this application of heat is repeated at regular intervals, it is possible to impede the regeneration of cancer cells and simultaneously kill most of them. Hyperthermia of this tyoe falls into two categories: general hyperthermia and local hyperthermia. In local hyperthermia, in which cancerous tissue and its surroundings are selectively heated, methods using electromagnetic waves, electromagnetic induction, or ultrasonic waves have been proposed.

Figure 1:
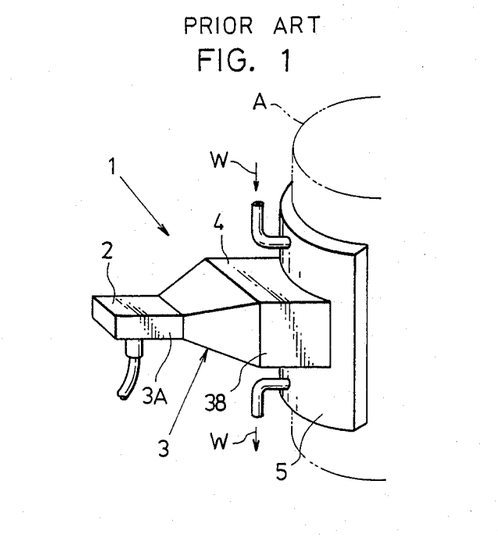
FIG. 1 is a perspective view of a conventional applicator, illustrating how it is used.
Figure 2:
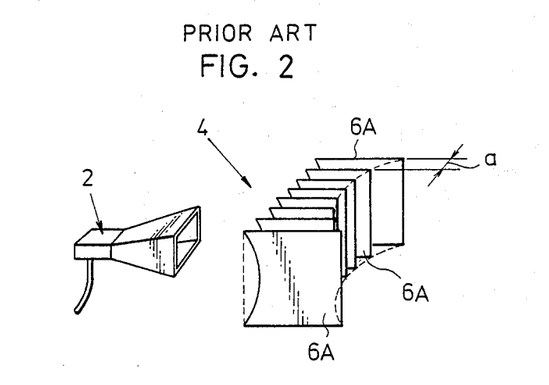
FIG. 2 shows the electromagnetic lens portion incorporated in the conventional applicator of FIG. 1.

Present inventors have proposed and are continuing to research the treanment of the cancers located deep in the human body by means of electromagnetic waves. In employing electromagnetic waves, it is necessary to focus the electromagnetic energy when transmitting the electromagnetic waves into the body. For this purpose, the present inventors have incorporated an electromagnetic lens in a heating applicator. An applicator 1 adopted by the present inventors, as shown in FIGS. 1 and 2, is composed of a casing 3 which functions as a waveguide, a wave supply portion 2 provided at one end of the casing 3, and an electromagnetic lens portions 4 provided at the other end of the casing 3. An output side of the electromagnetic lens portions 4 is provided with a solid cooling plate 5 which prevents the surface of the body from overheating, and which can be cooled by cooling water.

The electromagnetic lens portion 4 is constructed so that metal plates 6A, 6A are disposed at predetermined intervals a, as shown in FIG. 2. In order to convert spherical waves transmitted from the wave supply portion 2 into plane waves, the electromagnetic-reception edge of each metal plate 6A is concave over its entire vertical length, so that the plate outputs substantially completely plane waves. Metal plates of shorter lengths are disposed in the center portion of the array of metal plates 6A so that the entire electromagnetic-transmission sides of the array of metal plates 6A is concave in the direction which is perpendicular to the concave sides of the metal plates, as shown in FIG. 2, so as to focus one side of the plane waves which are formed by the concave edge of each metal plate.

However, this conventional applicator suffers from the following disadvantages:

(1) Since the electromagnetic waves are focused in only one direction, sufficient or efficient focusing is not available in the body.

(2) A plurality of different applicators must be provided in order to treat affected parts located at different depths. The most suitable applicator is selected from the plurality of applicators every time treatment is conducted, and it must then be mounted on a support mechanism, making the preparation time-consuming.

(3) A large number of applicators must be prepared, which makes the apparatus expensive.

SUMMARY OF THE INVENTION

An object of the present invention is to provide an applicator for use in hyperthermia which is capable of irradiating electromagnetic wave energy concentrated by an electromagnetic lens efficiently and continuously in a certain period of time to effectively treat cancerous tissue in the human body.

A further object of the present invention is to provide an applicator for use in hyperthermia which can be prepared quickly to suit various patients with easy handling.

A still further object of the present invention is to provide an applicator for use in hyperthermia which can efficiently treat a heated region in the human body with an electromagnetic wave supply having a relatively small output.

DETAILED DESCRIPTION

First Embodiment

A first embodiment of the present invention will now be described with reference to FIGS. 3 to 14.

Figure 3:
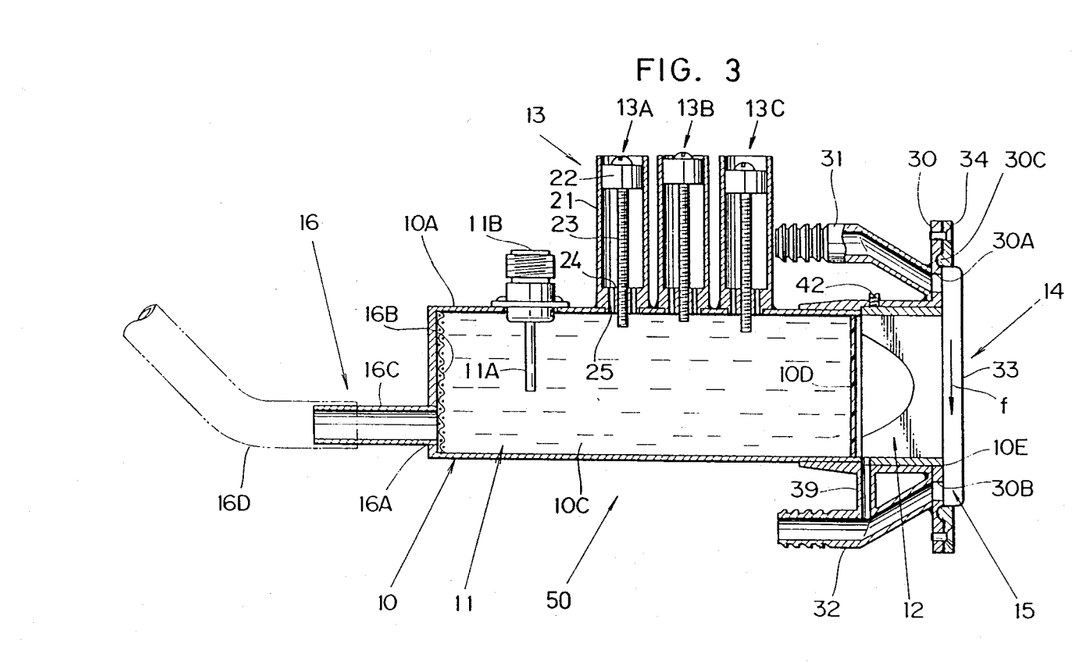
FIG. 3 is a sectional view of a first embodiment of the present invention.
Figure 4:
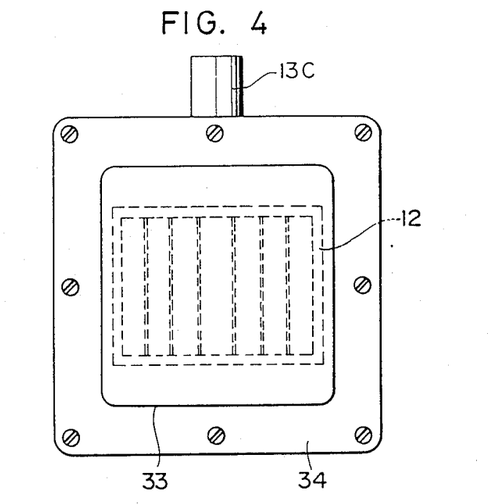
FIG. 4 is a side elevational view of the applicator shown in FIG. 3, as viewed from the right in FIG. 3.
Figure 5:
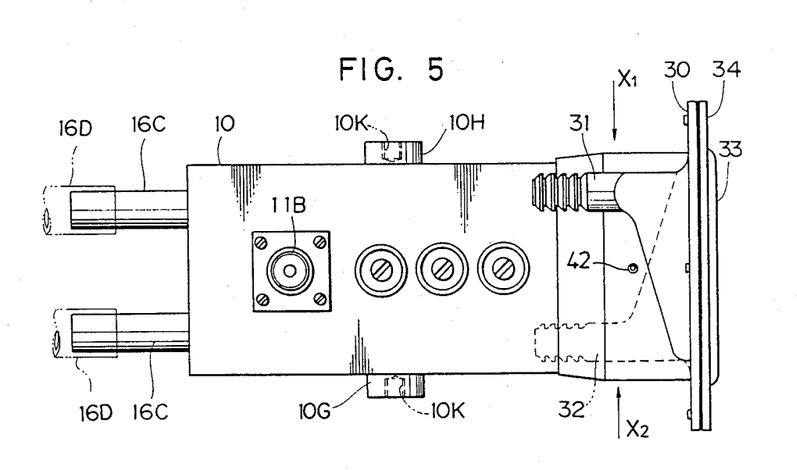
FIG. 5 is a plan view of the applicator shown in FIG. 3.
Figure 6:
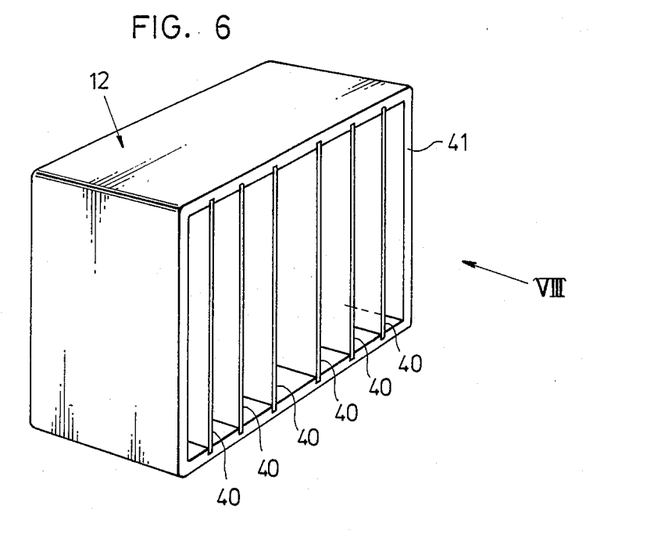
FIGS. 6 and 7 are perspective views of the electromagnetic lens portions emeployed in the applicator shown in FIG. 3.
Figure 7:
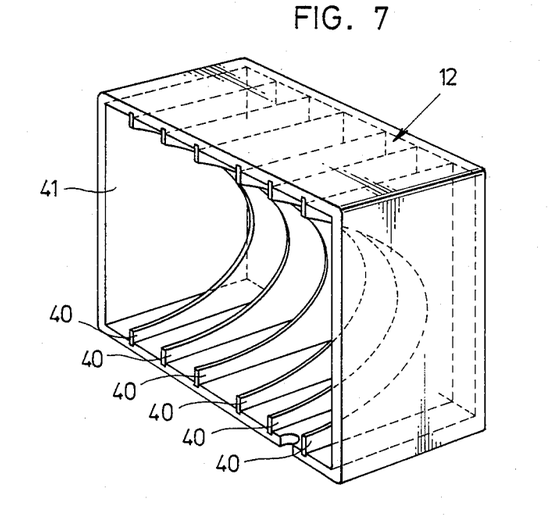

Referring first to FIG. 3, reference numeral 10 denotes a casing which functions as a waveguide. The casing 10, as shown in FIGS. 4 and 5, is in the shape of a box, and is provided with an electromagentic wave supply portion 11 at one end thereof, an electromagnetic lens portion 12 at the other end thereof, and a stub tuner mechanism 13 for tuning electromagnetic waves at an intermedicte portion thereof. The right end of the electromagnetic lens portion 12, as viewed in FIG. 3, forms an electromagnetic wave-radiating end portion 14 which is open. A cooling mechanism 15 for cooling the surface of the human body is provided in the electromagnetic wave-radiating end portion 14 in such a manner that it covers the end portion 14 from the outside.

The electromagnetic wave supply portion 11 includes a supply portion waveguide 10A which is a component of the casing 10, a driving antenna 11A protruding from the central portion of the supply portion waveguide 10A, and a waterproof coaxial connector 11B for electromagnetic waves which is connected to the driving antenna 11A. This construction ensures that electromagnetic waves transmitted through the coaxial connector 11B are efficiently introduced into the casing 10.

The supply portion waveguide 10A is filled with insulating oil (hereinafter referred to merely as "oil") 10C which has a small damping factor with respect to electromagnetic waves, including the portion where the stub tuner mechanism 13 is mounted. An oil sealing screen 10D made of a dielectric material is provided so as to seal in the oil 10C.

The stub tuner mechanism 13 of this embodiment employs three stub tuners disposed at predetermined intervals in alignment with each other. To be specific, stub tuners 13A, 13B, and 13C each include a cylinder portion 21 with one open end, a waterproof piston member 22 which moves back and forth in the cylinder portion 21, a screw member 23 which is integrally formed with the piston member 22 and which has a a stub-tuning function, a screw hole 24 through which the screw member 23 is threaded, and at least one through-hole 25 communicating the interiors of the casing 10 and the cylinder portion 21. Each screw member 23 is rotated so that it protrudes a suitable amount into the casing 10, thereby providing the required tuning.

In this case, the through-hole 25 constitutes a hole through which the oil 10C circulates as a result of the reciprocal motion of the piston member 22.

An oil release mechanism 16 is provided in a part of the supply portion waveguide 10A so as to enable the smooth circulation of the oil 10C. i.e., the smooth reciprocal motion of the piston members 22, as well as to enable thermal expansion of the oil due to overheating of the casing as a result of the continuous use thereof.

The oil release mechanism 16 of this embodiment includes through-holes 16A, 16A provided at two positions of the supply portion waveguide 10A at a predetermined spacing, wire mesh 16B which has a relatively small mesh size and which is disposed inside the supply portion waveguide 10A in such a manner that it covers the through-holes 16A from the inside, guide tubes 16C, 16C connected to the respective through-holes 16A, 16A, and oil release tubes 16D, 16D made of a relatively soft material which are connected to the respective guide tubes 16C, 16C and extend upward. The guide tubes 16C and oil release tubes 16D together constitute a fluid guide means. The wire mesh 16B forms part of the side wall of the electromagnetic wave supply portion 11. Therefore, it may be replaced with, for example, a plurality of small holes provided directly in the inner wall of the electromagnetic wave supply portion 11, if they can be made to function in the same manner.

A plate-like metal member having a large number of small through-holes may also be employed in place of the wire mesh 16B.

The cooling mechanism 15 provided at the electromagnetic wave-radiating end portion 14 of the casing 10 is made flat in order to be able to cool the surface of the heated portion efficiently. To be more specific, the cooling mechanism 15 includes a base plate 30 which is integrally secured to the casing 10, a rectangular coolant inlet 30A provided on one edge of the base plate 30, a corresponding rectangular coolant outlet 30B provided on the other edge of the base plate 30, an insulating film waterproofing groove 30C which is provided in such a manner that ir surrounds the coolant inlet and outlet 30A and 30B as well as an aperture 10E in the electromagnetic wave-radiating end portion 14, coolant guides 31 and 32 connected to the coolant inlet 30A and output 30B, respectively, a flat insulating member 33 disposed in such a manner that it covers substantially the entire surface of the electromagnetic wave-radiating end portion 14, and a frame plate 34 for mounting the insulating film member 33 onto the base plate 30 in a state wherein the periphery of the insulating film member 33 is waterproofed and the insulating film member can be easily removed. The insulating film member 33 is in the form of a dish with its outer side raised and its inner side open, and is made of a film-shaped dielectric which has a small damping factor with respect to electromagnetic waves. The cooling water which flows in through the inlet 30A moves over the inside of the insulating film member 33 and out through the outlet 30B, as shown by the arrow f in FIG. 3. During this time, it cools the surface of the body efficiently through the intermediary of the insulating film member 33.

The electromagnetic lens portion 12, provided at the right end of the casing 10 as viewed in FIG. 3, is formed into a box with two opposite sides, as shown in FIGS. 6 to 10. It is detachably housed in the casing 10.

Figure 8:
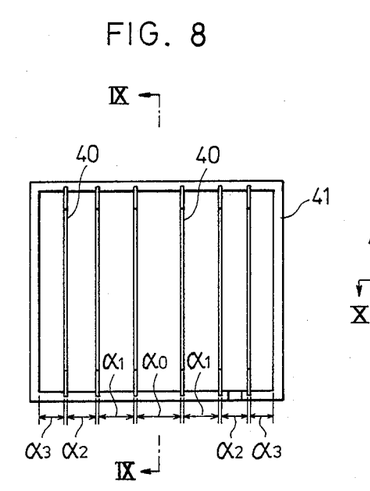
FIG. 8 is a front view of the electromagnetic lens portion, as viewed in the direction of the arrow VIII in FIG. 6.
Figure 9:
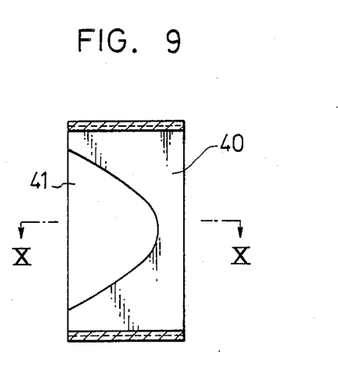
FIG. 9 is a section taken along the line IX—IX of FIG. 8.
Figure 11:
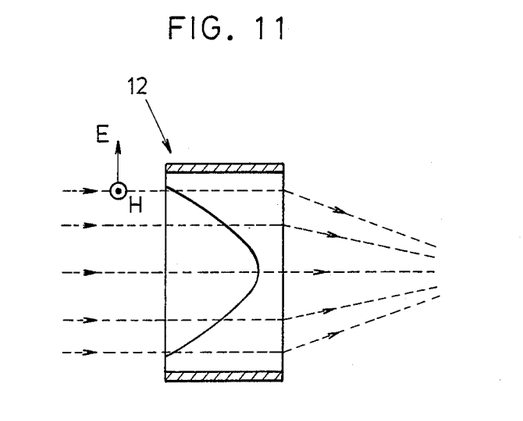
FIGS. 11 and 12 each illustrate how the electromagnetic waves are focused.
Figure 12:
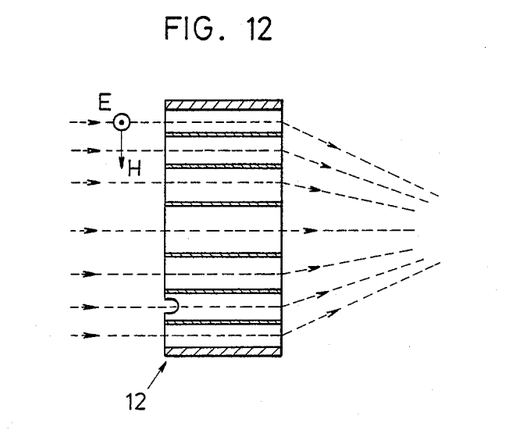
Figure 13:
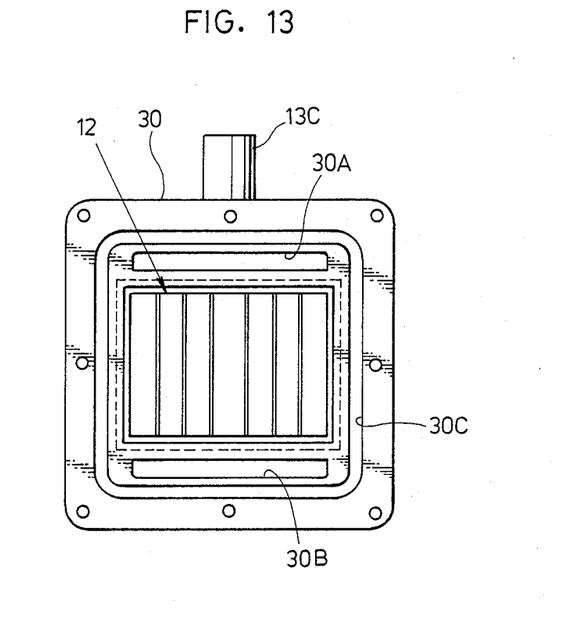
FIG. 13 is a side elevational view of the applicator shown in FIG. 3, with an insulating member removed and as viewed from the right side.

To be more specific, the electromagnetic lens portion 12 includes a plurality of metal plates 40, 40 of the same dimensions and a frame 41 for locking the upper and lower edges of the metal plates 40, as viewed in FIG. 8. The metal plates 40 are spaced apart from each other at intervals, as shown in FIG. 8, which are a maximum of $\alpha_0$ at the center and which become gradually smaller with a dimension of $\alpha_1$, $\alpha_2$, and $\alpha_3$ (where $\alpha_0 > \alpha_1 > \alpha_2 > \alpha_3$) closer to the side walls of the frame 41. This overall arrangement of the metal plates provides the received electromagnetic waves with a predetermined lens effect in one direction as shown by the dotted lines in FIG. 12. The central portion of the edge of each metal plate 40 which faces the electromagnetic wave supply portion 11 is cut out in an arcuate shape, so as to provide the same electromagnetic waves with a predetermined lens effects in another direction which is perpendicular to the first direction, as shown in FIG. 11. FIG. 13 shows the thus-arranged electromagnetic lens portion 12 accomodated in the casing 10, as seen when looking from the right side of FIG. 3 (with the insulating film member 33 remove therefrom). In this case, the electromagnetic lens portion 12 is open on both its electromagnetic wave reception and radiating sides so as to enable the coolant in the cooling mechanism 15 to easily flow into and out of the electromagnetic lens portion. The electromagnetic lens portion 12 is locked by means of a setscrew 42, as shown in FIG. 3. The box-shaped electromagnetic lens portion 12 is deteachably mounted, as previously described. An affected part may be located at any depth in the body, so several tens of lensa portions 12 are prepared beforehand, and a suitable lens portion is selected to suit the depth of the affected part to be treated.

The electromagnetic lens portion 12 is provided with a pipe 39 of a relatively small diameter, on the side thereof which faces the electromagnetic wave supply portion 11. The pipe 39 communicates with the coolant guide 32 for the coolant outlet 30B and acts as a bubble-releasing means through which bubbles generated during the treatment are directly sucked away through the coolant guide 32 by the vacuum pressure generated as the result of the flow of coolant.

Figure 14:
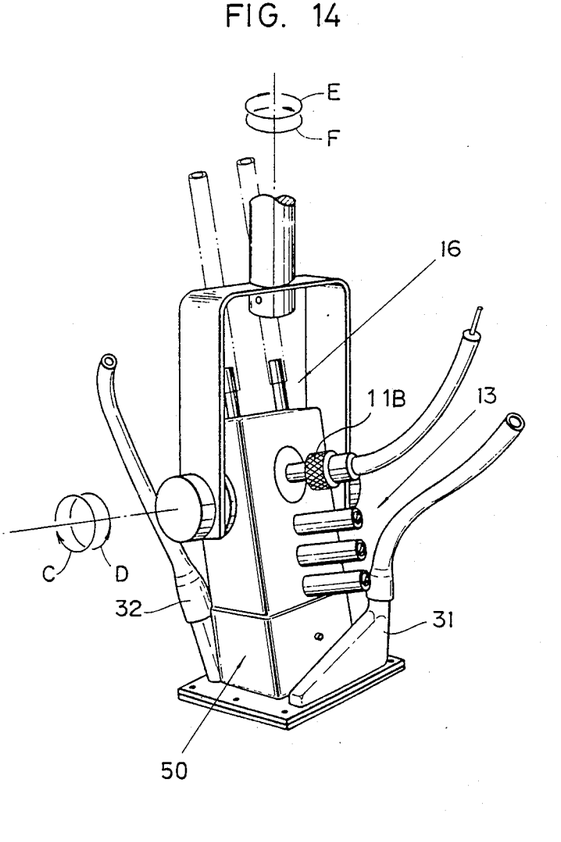
FIG. 14 is a perspective view of the applicator shown in FIG. 3, illustrating how it is mounted.
Figure 15:
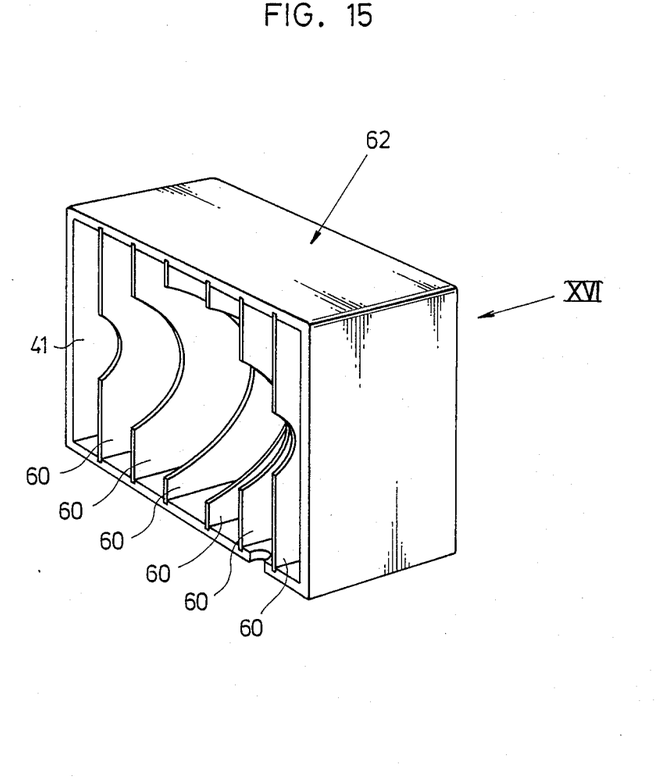
FIG. 15 is a perspective view of the electromagnetic lens portion of the applicator in a second embodiment.
Figures 16, 17:
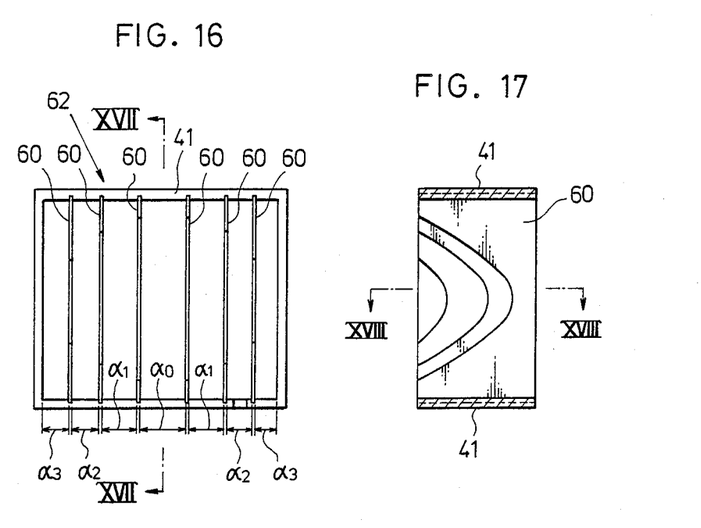
FIG. 16 is a front elevational view of the electromagnetic lens portion when looking from the direction shown by the arrow XVI of FIG. 15.
FIG. 17 is a section taken along the line XVII—XVII of FIG. 16.
Figure 18:
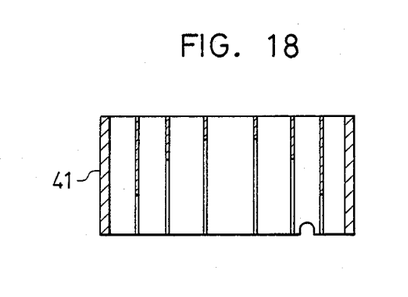
FIG. 18 is section taken along the line XVIII—XVIII of FIG. 17.

The thus-constructed applicator 50 of this embodiment for use in hyperthermia is retained by support members 10G and 10H provided at both sides thereof, in an applicator retaining means 51 which has an inverted-U shaped configuration, in such a manner that it can be pivoted freely, as shown by the arrows C and D in FIG. 14. The applicator retaining means 51 is supported by a support mechanism (not shown) so that it can be rotated as shown by the arrows E and f, thereby ensuring that the applicator can assume any position to suit the affected part being treated.

Operation of the first embodiment will now be described below.

The electromagnetic waves which are input through the coaxial connector 11B and output toward the inside of the casing 10 by the driving antenna 11A are transmitted to the electromagnetic lens portion 12 without being damped while propagating in the oil 10C. As they propagate through the electromagnetic lens portion 12, the waves passing through the outer portion moves faster than those passing through the central portion, so that they are focused at the same time that they are radiated from the electromagnetic lens portion 12. The electromagnetic waves which have been focused by the lens portion, after they pass through the cooling mechanism 15, propagate from the surface of the body toward the human body, with some of them being reflected by the surface of the body and the remaining ones acting to heat the body surface and deeper regions thereof. At this time, the surface of the body is efficiently cooled by the cooling mechanism 15. The point of focus at a predetermined depth and its surrounds can be effectively heated, since the electromagnetic waves are focused into a point through the omnidirectional lens effect imparted by the electromagnetic lens.

The reflection of the waves by the surface of the body is caused by the untuned impedance in the electromagnetic wave transmission system. Such variation in impedance is also generated at the reception side of the electromagnetic lens portion 12. In consequence, when from the driving antenna 11A, electromagnetic waves which have been reflected by both the electromagnic lens portion 12 and the heated body surface can be detected. In such a case, the impedance of the electromagnetic lens portion 12 and the heated portion can be immediately tuned by adequately adjusting the stub tuner mechanism 13. This prevents the generation of standing waves caused by the reflected electromagnetic waves, thereby preventing the applicator from overheating and efficiently transmitting electromagnetic energy into the heated portion of the body.

Impedance tuning with the stub tuner mechanism 13 is actually conducted by an operator by checking the reflection ratio which is displayed on the reflected wave displayed means (not shown) of a directional coupler connected to the coaxial connector 11B.

Apart from the impedance tuning effected by the stub tuner mechanism 13, a slight amount of energy loss is generated in the casing 10 due to the impedance of the electromagnetic wave transmission system. As a result, the casing 10 and the oil 10C are kept heated when the applicator is continuously used, thereby generating thermal expansion of the oil 10C. The expanded oil could damage the oil sealing screen 10D if left untreated. To cope with this problem, the oil release mechanism 16 acts to lead the thermally expanded portion of the oil 10C outside. The oil release mechanism 16 is also unable when replacing the oil 10C with new oil.

The electromagnetic lens portion 12 is so constructed that it can easily be replaced. Electromagnetic lens portions having different degrees of focusing are therefore selectively used to suit particular affected parts located at any depth within the human body, thereby enabling efficient hyperthermia.

In consequence, the applicator of the present invention makes a quick preparation operation possible when it is used for the treatment of various affected parts located at different depths, and sufficient heating time is thereby ensured. It is not necessary to prepare more than one of these applicators, and this makes the total cost of the apparatus used for hyperthermia relatively inexpensive.

The electromagnetic lens portion 12 of the applicator of the first embodiment employs the metal plates 40 having the same configuration. This makes the entire size of the lens portion 12 including the frame 41 small, thereby enabling in turn the reduction in size of the casing 10 and the applicator.

The first embodiment shows the applicator for heating a deep portion of the human body. However, the present invention is not limited to this type of applicator, and may be applied to an applicator for heating the surface of the human body by, for example, lowering the output of the applicator and moving the cooling mechanism 15.

Second Embodiment

Next, a second embodiment of the present invention will be described with reference to FIGS. 15 to 18.

In the first embodiment, the projected figures of the point of the focused electromagnetic waves are square in two directions. The second embodiment is intended to make them substantially circular.

More specifically, as shown by the figures, metal plates 60, 60 constituting an electromagnetic lens portion 62 are spaced apart from each other in the same manner as in the first embodiment at intervals which are a maximum of $\alpha_0$ at the center and which become gradually smaller with a dimension of $\alpha_1$, $\alpha_2$, and $\alpha_3$ (where $\alpha_0 > \alpha_1 > \alpha_2 > \alpha_3$) closer to the side walls, so as to provide an efficient lens effect in one direction.

On the other hand, the electromagnetic-reception side of each metal plate 60 is cut out in an arcuate shape with its vertical center serving as the center of the arch. In this case, the metal plate 60 having the maximum cut is located at the center of the lens portion, and the cut of the arch becomes smaller, the closer the metal plate is positioned to the side walls. Reference numeral 41 designates a similar frame to that employed in the first embodiment.

The applicator of the second embodiment is constructed in the same manner as that of the first embodiment, except for the above-described arrangement.

Thus, the applicator of this embodiment provides the same effect as that of the first embodiment. In addition to this, since the electromagnetic waves passing through the portion surrounded by each of the metal plates 60 constituting the electromagnetic lens portion 62 move faster, the cross-sectional shape of the focal point of the electromagnetic waves which are output from the electromagnetic wave-radiating end portion 14 is substantially circular. This can provide an efficient concentration of energy on a heated portion of the human body.

In the first and second embodiments, the electromagnetic lens portion 12 is mounted and removed from the side of the cooling mechanism 15. However, the present invention is not liminted to this, and the lens portion 12 may also be mounted and removed, for example, at the portion shown by $X_1$ and $X_2$ in FIG. 5 on the sides of the casing 10, if that portion is made into a square opening and this opening is adequately waterproofed. The casing 10 may be structured so that it is separable into the oil filled side and the electromagnetic lens portion side and the allow the electromagnetic lens portion 12 to be mounted on and removed from the electromagnetic lens portions side of the casing.

What is claimed is:

1. An applicator for use in hyperthermia comprising:
   (a) a casing having opposite, axial ends;
   (b) an electromagnetic wave supply portion mounted on one of said ends of transmitting into said toward the other of said ends, omnidirectional electromagnetic waves having electric and magnetic field components; and
   (c) an electromagnetic lens portion having spaced lateral sides and being mounted on said other of said ends for receiving, focusing, and transmitting said electromagnetic waves;
   (d) said lens portion including a plurality of laterally spaced, metal plates positioned parallel to said sides, the lateral spacing between said plates being non-uniform for deflecting both the electric and magnetic field components of the 2. An applicator according to claim 1 wherein the spacing between plates that are nearer the lateral sides of the lens is less than the spacing between plates that are more remote from said lateral sides.

3. An applicator according to claim 2 wherein the spacing between adjacent ones of said plates is a function of the distance of the plates from the axis of the lens.

4. An applicator according to claim 3 wherein the edge of each of said metal plates facing said electromagnetic wave supply portion is cut-out, the cut-outs being uniform and arcuate in shape.

5. An applicator according to claim 3 wherein the edge of each of said metal plates facing said electromagnetic wave supply portion is cut-out, the cut-outs being non-uniform.

6. An applicator according to claim 5 wherein the cut-outs are arcuate.

7. An applicator according to claim 6 wherein the size of the cut-outs in plates nearer the lateral sides of the lens is smaller than the size of the cut-outs in plates that are more remote from said lateral sides.

8. An applicator according to claim 1 wherein the lateral spacing between said plates is such that electromagnetic waves transmitted by the lens are deflected to a point.

9. An applicator according to claim 8 wherein wherein said point lies along the axis of said casing.

10. An applicator according to claim 1 wherein said lens portion is detachably mounted on said casing.

11. An applicator according to claim 1 wherein the edge of each of said metal plates facing said electromagnetic wave supply portion is cut-out.

12. An applicator according to claim 11 wherein the cut-outs in the edges of said plates are uniform.

13. An applicator according to claim 11 wherein the cut-outs in the edges of said plates are uniform and are arcuate in shape.

14. An applicator according to claim 11 wherein the cut-outs in the edges of said plates are non-uniform.

15. An applicator according to claim 11 wherein the cut-outs in the edges of said plates are non-uniform and are arcuate.

16. An applicator according to claim 15 wherein the size of the cut-outs in plates nearer the lateral sides of the lens are smaller than the size of the cut-outs in plates that are more remote from said lateral sides.

* * * * *

UNITED STATES PATENT AND TRADEMARK OFFICE
CERTIFICATE OF CORRECTION

PATENT NO. : 4,841,989　　　　　　　　　　　　　　　　Page 1 of 2

DATED    : June 27, 1989

INVENTOR(S) : M. KIKUCHI et al.

Figure 10:
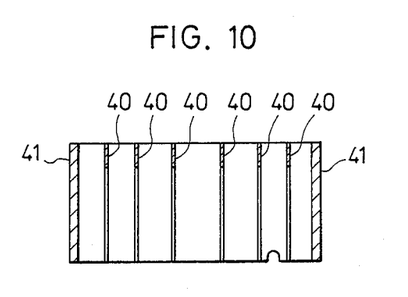
FIG. 10 is a section taken along the line X—X of FIG. 9.

It is certified that error appears in the above-identified patent and that said Letters Patent is hereby corrected as shown below:

Column 1, line 12 delete [2. Prior Art].
　　　Column 1, between lines 12 and 13, insert ---2. Prior Art---.
　　　Column 1, line 21 change "tyoe" to ---type---.
　　　Column 1, line 23 change "treantment" to ---treatment---.
　　　Column 1, lines 38/39 change "portions" to ---portion---.
　　　Column 1, line 40 change "portions" to ---portion---.
　　　Column 2, line 26 change "showns" to ---shows---.
　　　Column 2, line 35 change "emeployed" to ---employed---.
　　　Column 2, line 41 delete [Fig. 10 is a section taken along the line X-X].
　　　Column 2, line 42 delete [of Fig. 9;].
　　　Column 2, line 42 insert ---Fig. 10 is a section taken along the line X-X of Fig. 9;---.
　　　Column 2, line 57 insert ---a--- after "is".
　　　Column 3, line 4 change "intermedicte" to ---intermediate---.
　　　Column 3, line 35 change "a a" to ---a---.
　　　Column 4, line 14 change "ir" to ---it---.
　　　Column 4, line 55 change "effects" to ---effect---.
　　　Column 4, line 58 change "accomodated" to ---accommodated---.
　　　Column 4, line 60 change "remove" to ---removed---.
　　　Column 5, line 2 change "lensa" to ---lens---.

UNITED STATES PATENT AND TRADEMARK OFFICE
CERTIFICATE OF CORRECTION

PATENT NO. : 4,841,989

DATED : June 27, 1989

INVENTOR(S) : M. KIKUCHI et al.

It is certified that error appears in the above-identified patent and that said Letters Patent is hereby corrected as shown below:

Column 5, line 22 change "f" to ---F---.
Column 5, line 46 change "surrounds" to ---surroundings---.
Column 5, line 55 insert ---viewed--- before "from".
Column 6, line 1 change "displayed" to ---display---.
Column 6, line 14 change "unable" to ---usable---.
Column 7, line 18 change "liminted" to ---limited---.
Column 7, line 25 change "the" to ---to--- before "allow".
Column 7, line 27 change "portions" to ---portion---.
Column 7, line 32 change "of" to ---for--- before "transmitting".
Column 7, line 32 insert ---casing--- before "toward".
Column 7, line 44 after "the" insert ---radiated electromagnetic waves in a lateral direction---.
Column 8, lines 26/27 change "wherein wherein" to ---wherein---.

Signed and Sealed this

First Day of October, 1991

Attest:

HARRY F. MANBECK, JR.

Attesting Officer

Commissioner of Patents and Trademarks